United States Patent
Codner et al.

[11] Patent Number: 5,955,887
[45] Date of Patent: *Sep. 21, 1999

[54] IMPEDANCE TYPE ICE DETECTOR

[75] Inventors: Gerald Willey Codner, Ithaca, N.Y.;
Daniel A. Pruzan, Santa Clara, Calif.;
Richard Lawrence Rauckhorst, III,
North Canton, Ohio; **Allen Donald
Reich, Akron, Ohio; David Bert Sweet**,
Canal Fulton, Ohio

[73] Assignee: The B. F. Goodrich Company,
Richfield, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/770,923

[22] Filed: Dec. 20, 1996

Related U.S. Application Data

[60] Provisional application No. 60/009,159, Dec. 22, 1995.

[51] Int. Cl.⁶ .................................................. G01R 27/22
[52] U.S. Cl. ........................... 324/689; 324/687; 324/690; 324/679; 324/665
[58] Field of Search ..................................... 324/664, 671, 324/687, 688, 689, 690, 665, 679

[56] References Cited

U.S. PATENT DOCUMENTS

| | | |
|---|---|---|
| 2,432,669 | 12/1947 | Kliever . |
| 3,277,459 | 10/1966 | Werner . |
| 4,446,424 | 5/1984 | Chatanier ................................ 324/709 |
| 4,688,185 | 8/1987 | Magenheim et al. . |
| 4,765,187 | 8/1988 | Weinstein . |
| 4,766,369 | 8/1988 | Weinstein ................................ 324/670 |
| 5,093,626 | 3/1992 | Baer ........................................ 324/671 |
| 5,134,380 | 7/1992 | Jonas ....................................... 324/663 |
| 5,175,505 | 12/1992 | Magenau ................................ 324/671 |
| 5,191,791 | 3/1993 | Gerardi et al. . |
| 5,195,046 | 3/1993 | Gerardi et al. . |
| 5,206,806 | 4/1993 | Gerardi et al. . |
| 5,394,340 | 2/1995 | Inkpen et al. . |
| 5,398,547 | 3/1995 | Gerardi ................................... 324/671 |
| 5,523,959 | 6/1996 | Seegmiller ............................. 324/654 |
| 5,551,288 | 9/1996 | Geraldi ................................... 324/671 |
| 5,569,850 | 10/1996 | Rauckhorst, III . |
| 5,621,332 | 4/1997 | Inkpen et al. . |

*Primary Examiner*—Josie Ballato
*Assistant Examiner*—Jose M. Solis
*Attorney, Agent, or Firm*—Richard A. Romanchik

[57] ABSTRACT

An ice detector includes a pair of electrodes connected by a pair of leads to a control unit which measures the total impedance between leads to thereby sense and detect the presence of ice and other contaminants formed on top thereof utilizing a comparator circuit. The electrodes are integrated into patch which can be placed at different locations on an aircraft.

6 Claims, 13 Drawing Sheets

IMPEDANCE TYPE ICE DETECTOR

This application claims benefit under 35 U.S.C. §119(e) of U.S. Provisional Application 60/009,159, filed Dec. 22, 1995.

TECHNICAL FIELD

The present invention relates to ice detectors, and more particularly, to a total impedance type ice detector patch for aircraft surfaces.

BACKGROUND OF THE INVENTION

Under certain operating conditions, aircraft are vulnerable to the accumulation of contaminants on external component surfaces or skins. Examples of such contaminants include ice, water, and mixtures thereof. If left unchecked, the accumulation of ice can eventually so laden the aircraft with additional weight and so alter the airfoil configuration as to cause undesirable flying conditions. The ability to detect the accumulation of ice on such surfaces, and the ability to measure the accumulated thickness thereof so as to identify dangerous flight conditions, has therefore become highly desirable.

A number of different kinds of contaminant detectors have been utilized for such objectives. Among them are capacitive ice detectors, examples of which can be found in U.S. Pat. Nos. 4,766,369 to Weinstein, 5,191,791 to Gerardi et al. and 5,398,547 to Gerardi et al., both of which are hereby incorporated herein by reference.

The Weinstein and Gerardi patents are capacitive type ice detectors. That is, they detect the presence of ice and measures the ice's thickness by measuring changes in capacitance across a pair of spaced electrodes (located flush to the airfoil surface) due to the presence of ice on the airfoil surface between the electrodes.

Figure 1:
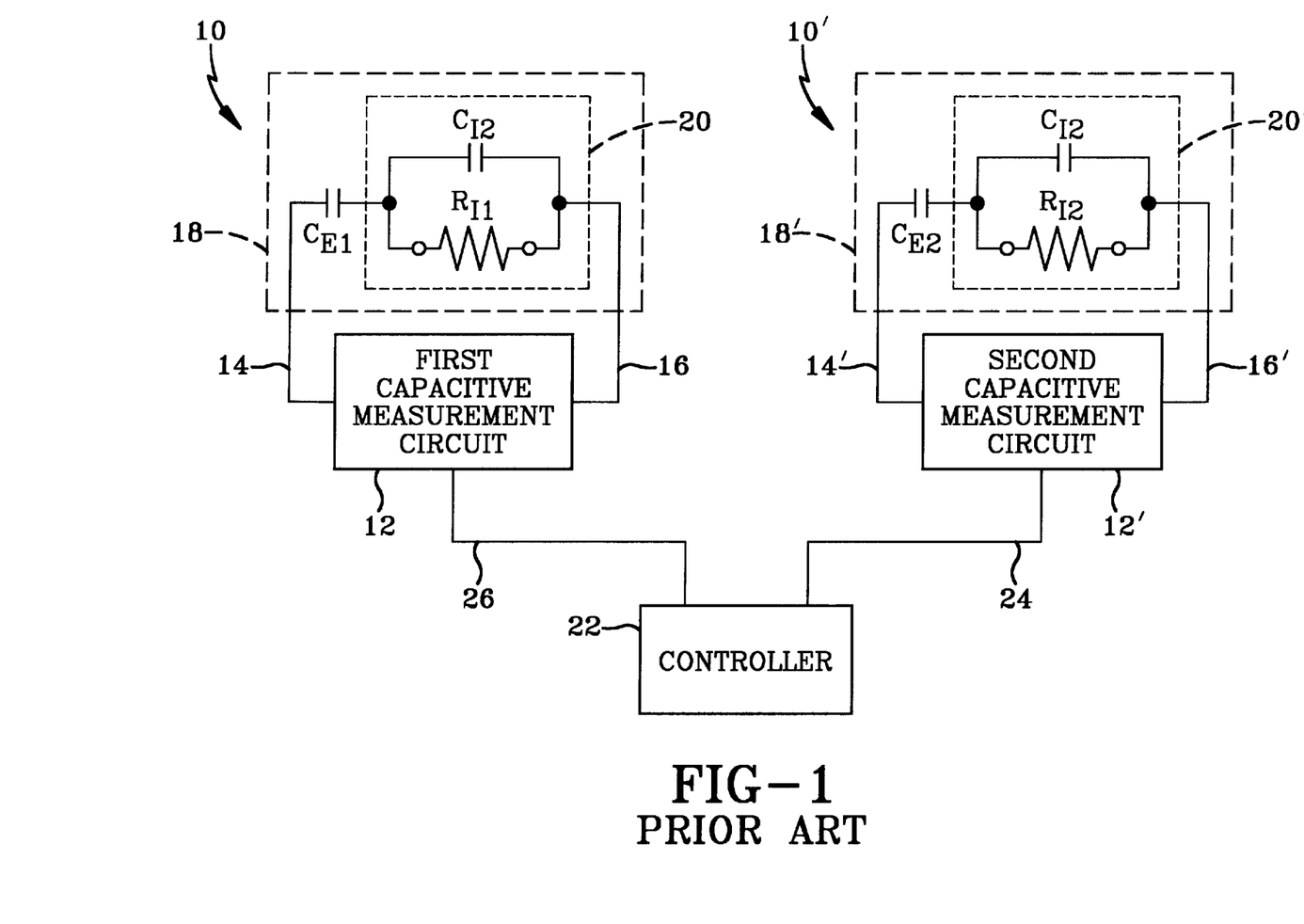
FIG. 1 is a schematic diagram of a prior art capacitive ice detector.

FIG. 1 is a schematic diagram of an ice detector 10 according to the prior art, including the Weinstein and Gerardi patents. A plurality of capacitance measuring circuits 12, 12' measure the capacitance across a pair of leads 14, 16, 14', 16', respectively, which are connected to a pair of electrodes (not shown). The electrodes and ice can be modeled as RC circuits 18, 18'. Capacitor $C_{E1}$, $C_{E2}$ represent the polarization capacitance across the electrodes. RC circuits 20, 20' are circuit models of the ice between the electrodes, and are comprised of a Resistor $R_{I1}$, $R_{I2}$ in parallel with a capacitor $C_{I1}$, $C_{I2}$. A controller 22 is connected to leads 24 and 26 and interprets the outputs of capacitance measuring circuits 12, 12'. Controller 22 may perform such functions as measure the ratio of capacitance detected by the circuits 12, 12' (as disclosed by Weinstein) or use a computer program to "resolve" ice thickness in some other way (as in Gerardi). One of the techniques suggested for this is to use neural networks and store large data files with capacitance signal profiles of the many different types of contaminants and many different types of ice. Capacitance is then measured and the contaminant classified using the stored data.

Pure ice is relatively nonconductive. $R_I$ is therefore large and the capacitance measurement circuits are effective in reading $C_I$.

A drawback to the prior art capacitive type detectors is that contaminants other than ice, such as water, are highly conductive. $R_I$ therefore becomes very small and the capacitance measurement circuits are not effective in reading $C_I$. Also, water causes changes in the overall capacitance across the electrodes similar to changes caused by ice. Since water and glycol by themselves do not create hazardous flying conditions, it is imperative to be able to distinguish between ice and other contaminants. To this end, it is also necessary to be able to identify the presence of ice on top of a layer of water. Because of the aforementioned capacitance measurement problems, Weinstein and Gerardi distinguish between water and ice by either utilizing a temperature probe in conjunction with their capacitive ice detectors, or by changing the stimulation frequency of the capacitance measurement circuit.

Efforts to improve ice detection systems have led to continuing developments to improve their cost, manufacturability, reliability, usefulness, and efficiency.

DISCLOSURE OF THE INVENTION

An object of the present invention is to provide an impedance type ice detector which measures overall impedance between electrodes to detect and measure ice.

According to the present invention, an ice detector includes: a pair of spaced electrodes disposed at the surface, said electrodes having a length being arranged substantially parallel to the plane of the surface; and, an impedance measurement device for measuring the impedance across said electrodes.

According to another aspect of the present invention, a method of making an ice detector includes the steps of providing a pair of spaced electrodes at the surface, said electrodes having a length being arranged substantially parallel to the plane of the surface; and, measuring the impedance across said electrodes.

The present invention provides a highly sensitive ice detector which is easy to manufacture, is highly reliable, is low cost, and is retrofittable onto existing aircraft.

These and other objects, features and advantages of the present invention will become more apparent in the light of the detailed description of exemplary embodiments thereof, as illustrated by the drawings.

BRIEF DESCRIPTION OF THE DRAWINGS

FIG. 12b is a schematic diagram representing the electrical circuit illustrated in FIG. 12a.

BEST MODE FOR CARRYING OUT THE INVENTION

Figure 2:
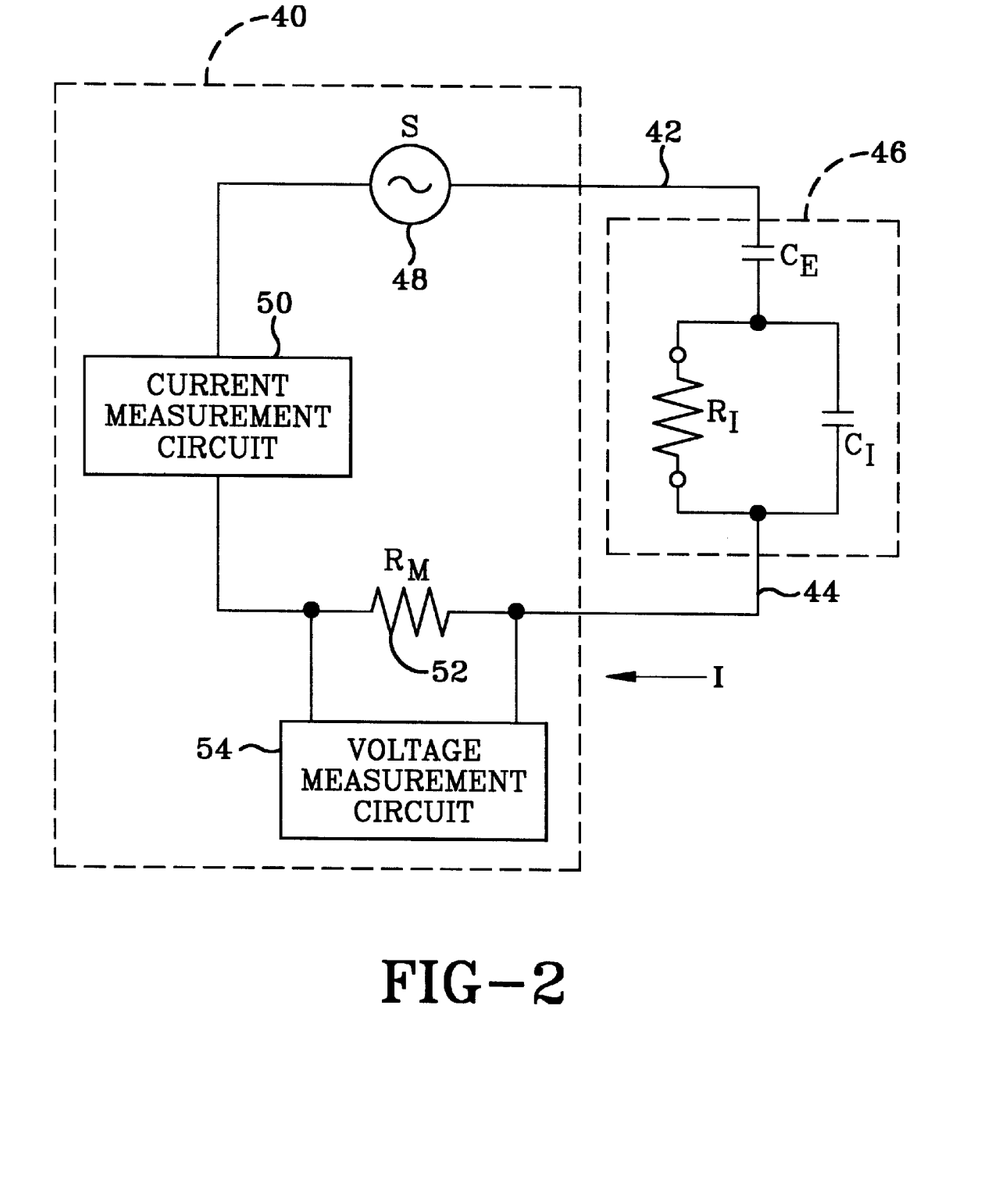
FIG. 2 is a schematic diagram of an impedance ice detector in accordance with the present invention.

Referring now to FIG. 2, wherein a schematic diagram in accordance with the present invention is illustrated. An impedance measurement circuit 40 is connected by leads 42, 44 to a pair of electrodes (not shown) for measuring ice, represented by model RC circuit 46. The electrodes are a pair of conductive strips spaced apart and located at the surface of the airfoil. Circuit 40 measures the total impedance across the electrodes. In the example of FIG. 2, a signal generator 48 supplies current through the electrodes and ice. The impedance across leads 42, 44 is calculated by either measuring current directly with a current measuring circuit or by measuring the voltage across a current sensing resistor with a voltage measurement circuit 54. The amount of current flowing through leads 42 and 44 is a function of the impedance therebetween.

The present impedance measurement ice detection and measurement device provides an improvement over prior art capacitive measurement ice detection devices because it can distinguish ice from water reliably and also it can measure ice thickness even though the ice may reside over a layer of water.

Figure 3A:
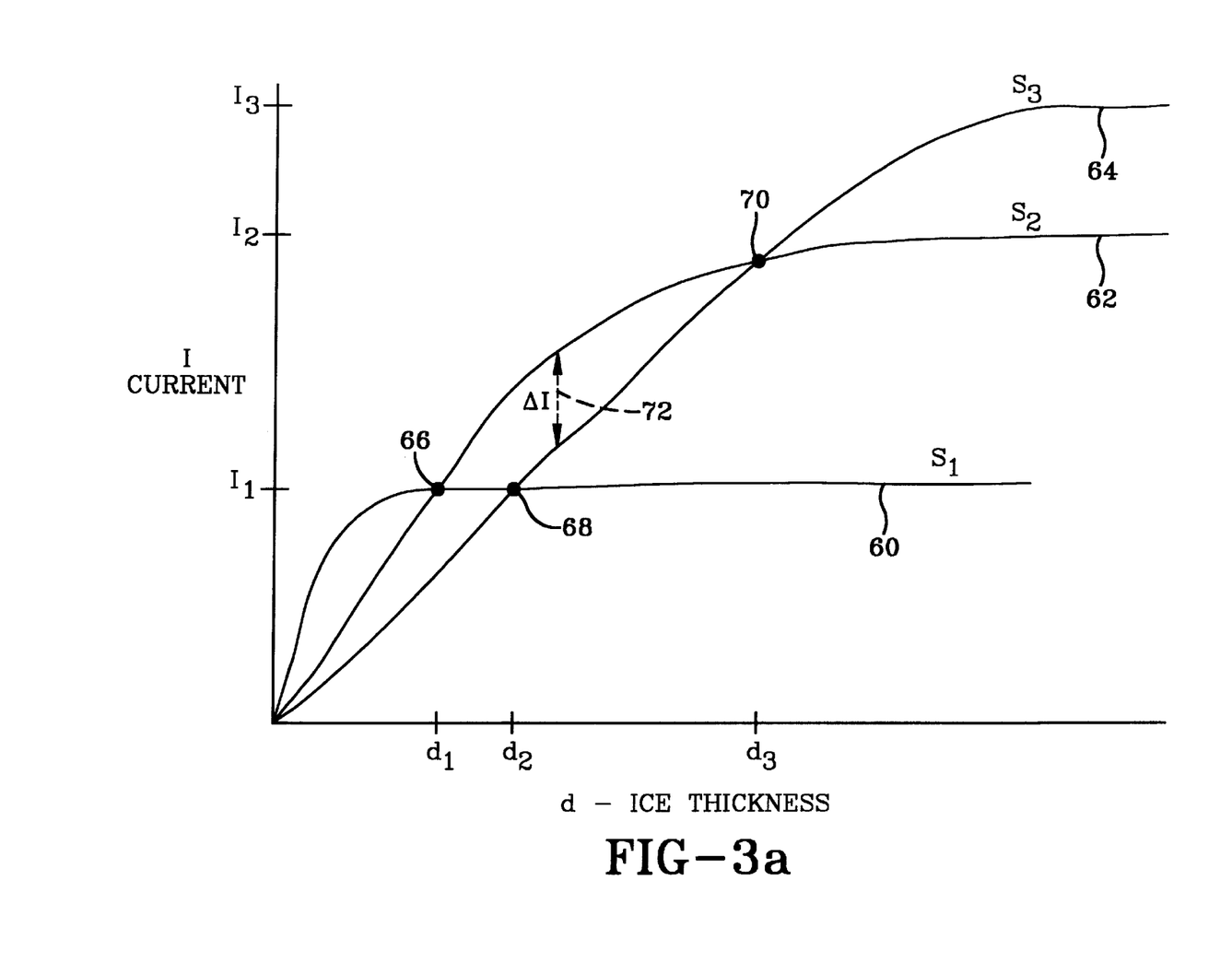
FIG. 3*a* is a graph showing the response of the ice detector of FIG. 2 for varying ice thickness.

Referring now to FIG. 3a, wherein a graph of the current flow I (through the circuit illustrated in FIG. 2 and measured by the impedance measurement ice detector of the present invention) versus ice thickness is depicted. A set of curves 60, 62, 64 illustrate typical response for three ice detectors, each detector having a pair of electrodes separated by a given spacing $S_1$, $S_2$, $S_3$, respectively, where $S_3 > S_2 > S_1$. It can be seen that the current of curves 60, 62 and 64 saturate out at values $I_1$, $I_2$, and $I_3$, respectively. The slopes of the current curves are approximately linear before the saturation level. Curves 60 and 62 intersect at a point 66, which correlates to a specific ice thickness $d_1$. Likewise intersection points 68 and 70 correlate to specific ice thickness's of $d_2$ and $d_3$.

The delta current ($\Delta I$) between curves 62 and 64 is represented by line 72. $\Delta I$ between the curves varies as ice thickness varies. Referring to curves 62 and 64, for ice thickness's below $d_3$, the value of current for curve 64 is always below the value of current for curve 62. The converse is true for ice thickness's above $d_3$. A simple determination can be made of whether the thickness of ice is below, equal to, or above $d_3$ by comparing the current flowing in the $S_3$ detector circuit to the current flowing in the $S_2$ detector circuit. For ice thickness below $d_1$, the current in the $S_1$ circuit will be above the current in the $S_2$ circuit. For ice thickness above $d_2$, the current in the $S_1$ circuit will be below the current in the $S_2$ circuit.

Figure 3B:
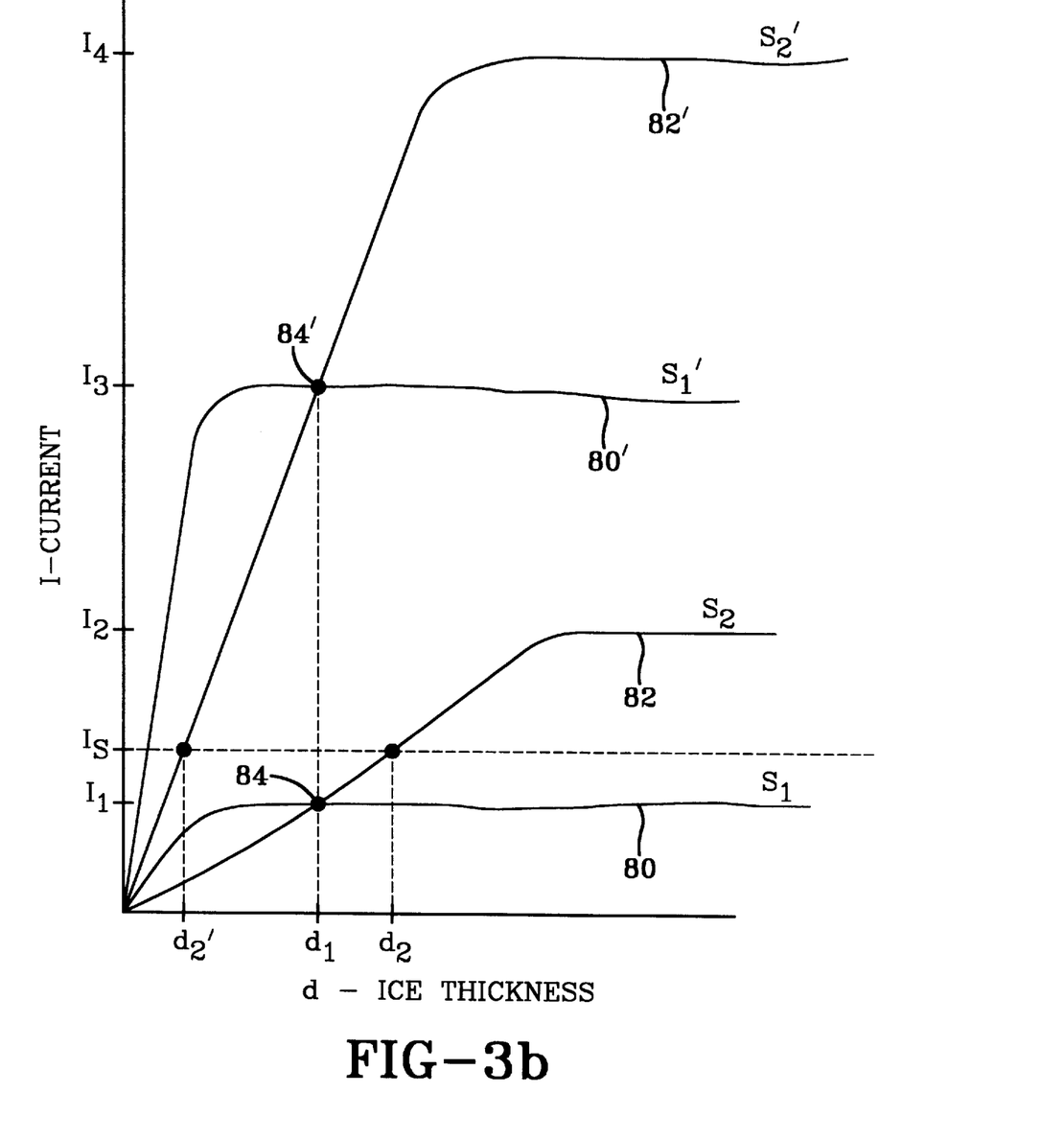
FIG. 3*b* is a graph showing response of the ice detector of FIG. 2 for varying ice thickness.

Referring now to FIG. 3b, wherein a graph of the current flow I (through the circuit illustrated in FIG. 2 and measured by the impedance measurement ice detector of the present invention) versus ice thickness is depicted. A set of curves 80, 82 illustrate typical response for two ice detectors, each detector having a pair of electrodes separated by a given spacing $S_1$, $S_2$, respectively, where $S_2 > S_1$. It can be seen that the current of curves 80, 82 saturate out at values $I_1$, and $I_2$, respectively. The slopes of the current curves are approximately linear before the saturation level. Curves 80 and 82 intersect at a point 84, which correlates to a specific ice thickness $d_1$. A set of curves 80' and 82' illustrate a typical response of the same ice detectors $S_1$ and $S_2$, but wherein the conductivity of the ice is greater than that for curves 80 and 82. The conductivity of the ice is a function of the liquid water content of the ice. Ice with a higher liquid water content than that of curves 80, 82 (and being more conductive) is represented by curves 80' and 82'. The intersection points 84 and 84' occur generally at the same ice thickness $d_1$. The present invention is therefore an improvement over prior capacitive ice detectors in that the thickness measurement technique of the present invention is insensitive to the liquid water content of ice. Prior capacitive ice detectors cannot measure wet ice because the capacitance across the electrodes is difficult if not impossible to measure due to the low resistance between electrodes. It is to be noted, however, that the conductivity of ice is also a function of the way water is dispersed within the ice. The term used to describe the dispersion of water within the ice hereinafter is uniformity. The curves illustrated in FIGS. 3a and 3b will therefore vary in accordance with the uniformity of the ice. Intersection points 66, 68, 70, 84 and 84' may be shifted if the ice is nonuniform or nonheterogenous. The electrodes of the present invention must therefore be configured and located for optimal measurement results.

It is to be noted that the intersection of curves S2 and S2' with a specific current level or threshold $I_5$, occur at different thickness points. The lower conductive ice S2 will provide higher thickness reading of d2 and the higher conductive ice s2' will provide a lower thickness reading d2'.

Ice can be detected and its thickness determined more effectively by measuring the amount of current flowing in an electrode type ice detection circuit. Since the current flow is a function of impedance, the present invention is an impedance ice detection apparatus. This impedance measurement technique provides an ice detection system greatly simplified over prior art systems, as will be described in further detail hereinafter.

It is to be further noted that the intersection point 70 occurs before both curves 62 and 64 have reached saturation. Ice detection and measurement can be accomplished effectively without having to saturate out the electrodes giving the present invention more measurement flexibility than prior systems. Prior capacitive type ice detectors required saturation of the circuit for their measurement techniques, which means only a limited number of data points could be gathered during a detection query cycle.

Figure 4:
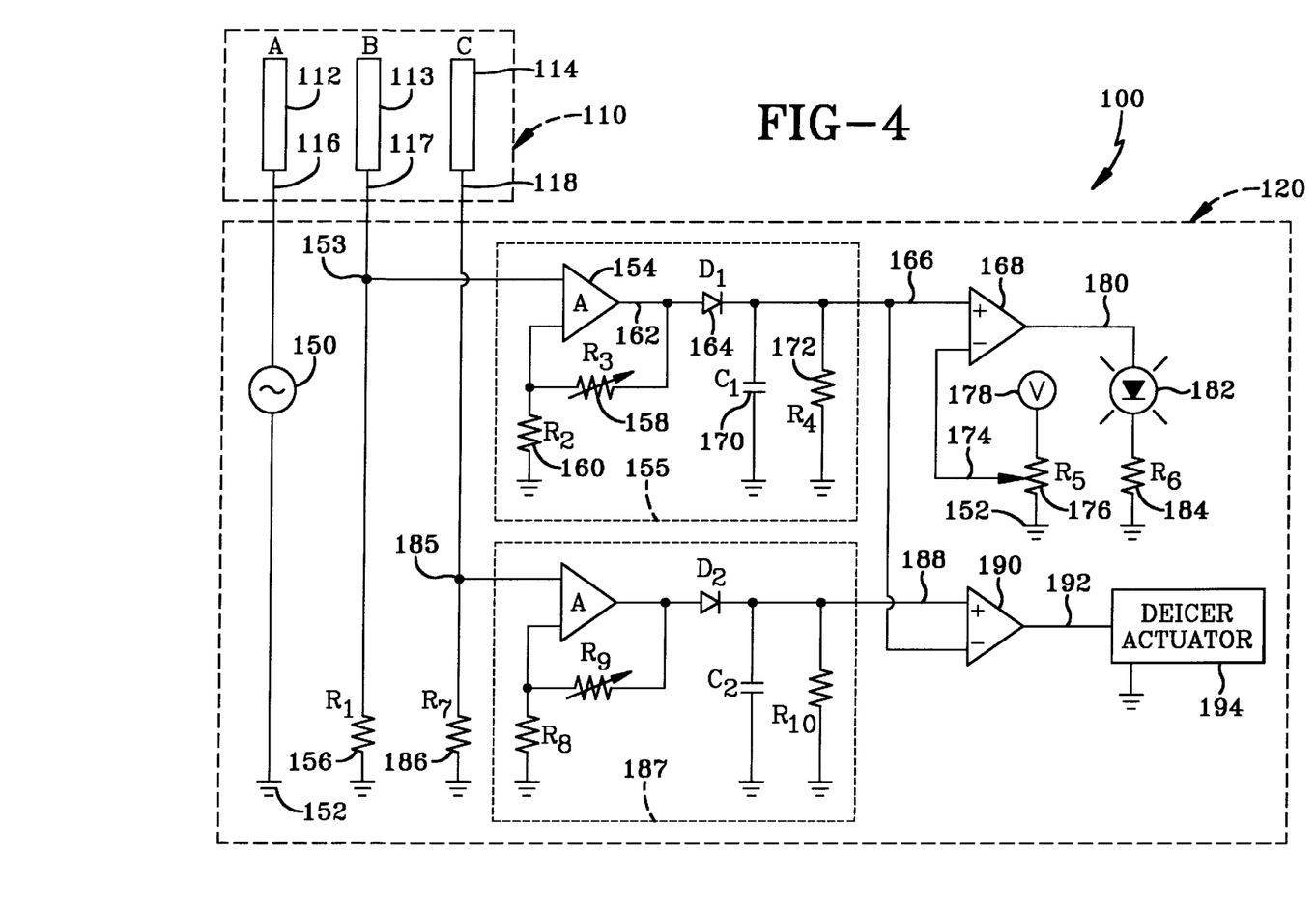
FIG. 4 is a generalized schematic diagram of a three electrode ice detection system in accordance with the present invention.

Referring now to FIG. 4, where a more detailed embodiment of an ice detector 100 in accordance with the present invention includes three electrodes (or elements) 112–114 connected by leads 116–118 to a controller means or control unit 120. Control unit 120 measures the impedance between leads 116 and 117 and the impedance between leads 116 and 118.

Lead 116 is connected to a signal generator 150, which is connected also to ground 152. Lead 117 is connected to a junction 153 between a resistor 156 and an amplification/filter stage 155. Lead 117 is connected to the plus input of a first operational amplifier or comparator 154. Amplifier 154 amplifies the signal on line 117 by the ratio of a pair of resistors 158, 160. The output of amplifier 154 is connected by a line 162 to a diode 164 which passes the signal on a line 166 to the plus input of an operational amplifier or comparator 168. A capacitor 170 and resistor 172 filter the signal on line 166 appropriately. The minus input of comparator 168 is connected by a line 174 to the wiper of a variable resistor 176. The variable resistor is connected between a voltage source 178 and ground 152. The output of comparator 168 is connected by a line 180 to a LED 182, which connected to a current limiting resistor 184. Lead 118 is connected to a node 185 between a resistor 186 and an amplification/filter stage 187 similar to amplification/filter stage 155 to amplify and filter the signal at node 185. The output of stage 187 is provided on a line 188 to the plus input of an operational amplifier or comparator 190. The minus input of comparator 190 is connected to signal on line 166. The output of comparator 190 is provided on a line 192 to a deicer actuator controller 194 for activating deicers (not shown in FIG. 4).

Operation of the ice detector 100 is as follows. Signal generator 150 applies a voltage to electrode 112. Current thereafter flows through electrode 113 and resistor 156. The voltage present at node 153 and the plus input of comparator 154 is therefore a function ($I \cdot R_{156}$) of the current flowing through electrode 113. The voltage signal at node 153 is amplified and filtered and compared by comparator 154 with a predetermined level set by adjusting variable resistor 176. If: a) the spacing between electrodes 112 and 113 is set so that the current flow therebetween reaches a level with a minimum ice thickness; and b) the voltage level at the minus input of comparator 168 is set to be equal to that saturation current value multiplied by the amplified signal on line 166; then comparator 168 turns LED 182 on when ice between the electrodes accumulates to the minimum thickness. In this way, the circuit 120 is utilized as a simple, inexpensive, but very effective ice detector.

It is to be noted that circuit 120 does not illuminate LED 162 with the presence of only water because, during flight, water cannot accumulate to a sufficient thickness to conduct enough current to sufficiently raise the voltage at node 153. This water insensitivity characteristic of the present invention provides an advantage over the prior art ice detectors because the temperature probes or frequency changes heretofore utilized are no longer necessary.

The current flowing between electrodes 112 and 114 is detected at node 185 by circuit 187. The conditioned signal out of circuit 187 is compared to the conditioned signal out of circuit 155 by comparator 190. The parameters of the two systems are set so that comparator 190 activates the deicer actuation controller 194 when ice has accumulated to a predetermined thickness. In this manner, the present invention can be utilized as a simplified but effective deicer actuation device.

Figure 5A:
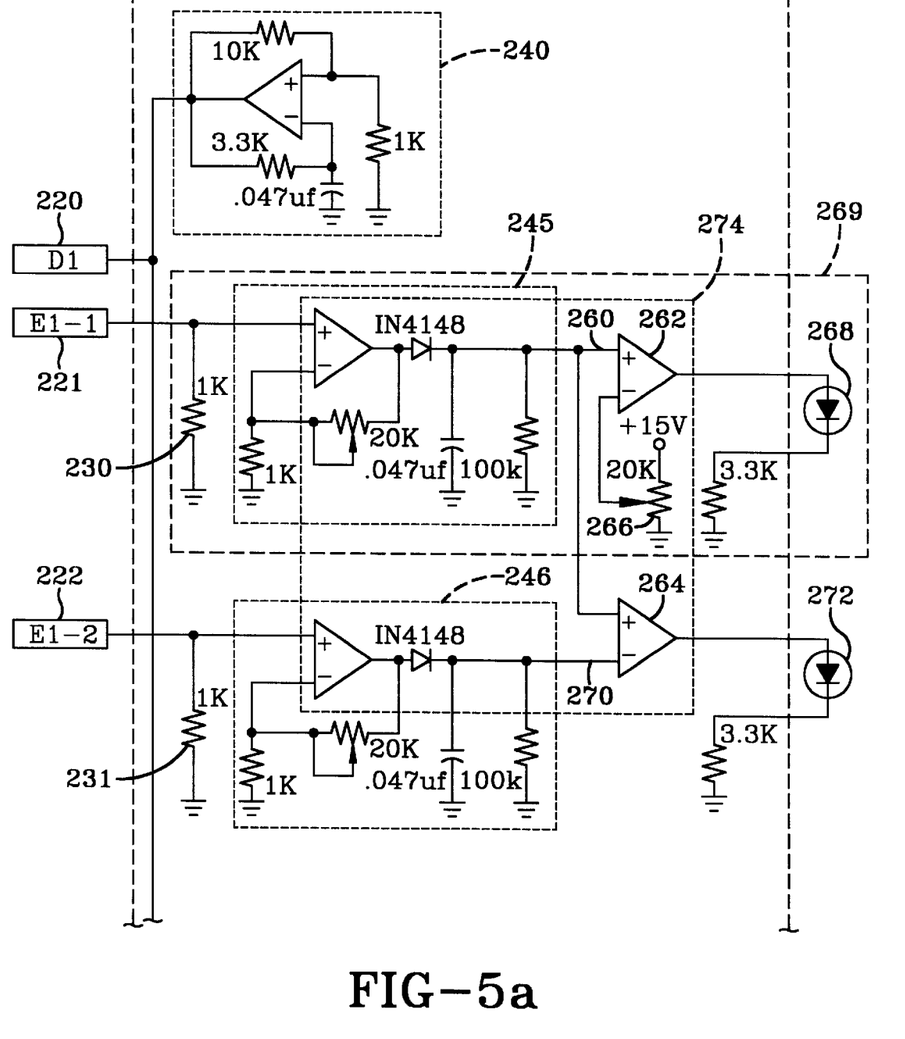
FIG. 5 is a detailed schematic diagram of a multiple electrode ice detection system in accordance with the present invention.
Figure 5B:
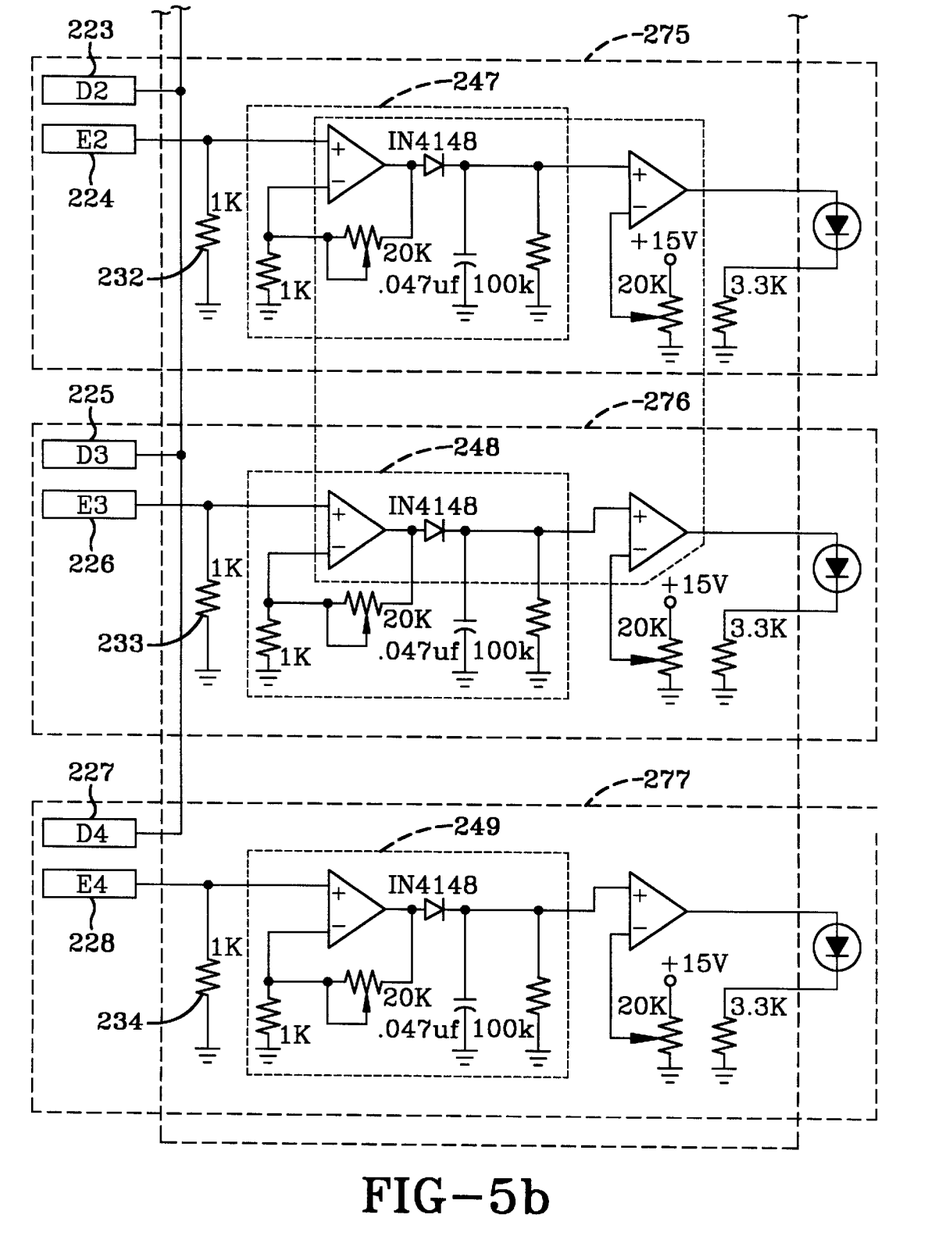

Referring now to FIG. 5, wherein an ice thickness measurement device in accordance with the present invention includes a plurality of electrodes 220–228 located at or near the airfoil surface. A signal generator 240 is connected to electrodes 220, 223, 225, and 227. Signal generator 240 preferably provides an approximately 12 volt peak to peak, 2500 Hz signal. Electrodes 221, 222, 224, 226, and 228 conduct part of the signal through respective 1 kΩ resistors 230–234. The consequential voltage across resistors 230–234 is provided to respective identical amplifier circuits 245–249 for isolation and amplification. The output of amplifier 245 is provided on a line 260 to the plus inputs of comparators 262 and 264. Comparator 262 compares the voltage on line 260 with the voltage at the tap of a resistor 266, the value of which is selected so that comparator 262 turns on LED 268 when a specific thickness of ice accumulates, as discussed previously. Circuit 269 therefore functions as a minimum ice thickness detector, or an ice/no ice detector.

Comparator 264 compares the voltage on line 260 with the voltage on line 270, which is determined from the current through electrode 222. The spacing between electrode 222 and electrode 220 is greater than the spacing between electrode 221 and 220. Comparator 264 turns on LED 272 when enough ice has accumulated that sufficient current flows through electrode 222 to cause a large enough differential at comparator 264. Circuit 274 therefore provides information that the thickness of ice is greater than that which caused LED 268 to illuminate. Those skilled in the art therefore appreciate that the present invention can be utilized as an ice thickness measurement device.

Circuits 275, 276, 277 operate in a similar fashion as circuit 269 does to provide ice/no ice detectors. The respective electrode pairs 223-224, 225-226, 227-228, however, are located at different places on the airfoil to ice location capabilities.

It will also be apparent to those skilled in the art that the present invention provides an improvement over prior art capacitive systems because a reliable, accurate system can be constructed using simple circuits which utilize basic electronic components which are widely available. As shown, microprocessors and other sophisticated equipment is unnecessary.

Figure 6:
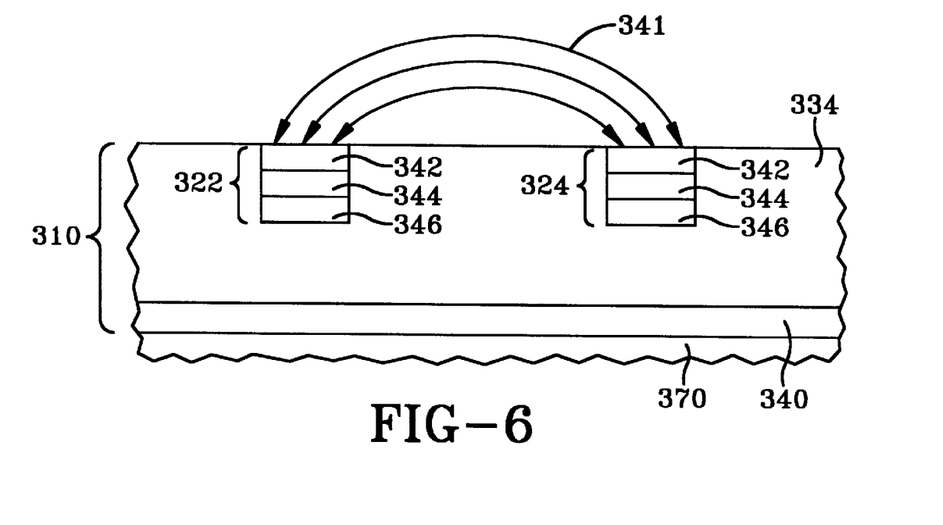
FIG. 6 is a cross sectional view of ice detector electrodes in an ice detection patch.

Referring now to FIG. 6, electrodes 330, 332 such as those described hereinbefore, are integrated into a resilient (or elastomeric) ice detection patch 334 described in greater detail hereinafter. Patch 334 may be attached or bonded to an airfoil 370 or other substrate. It is to be noted that other electrode configurations not explicitly shown herein may be utilized in the present invention. Ice detector 310 includes a non-conductive patch 334 disposed over a guard layer 340. Guard layer 340 is utilized to minimize stray capacitance by eliminating electric field lines between the electrodes and the airfoil surface 370. Lines 341, between electrodes 322 and 324, represent either field lines in the case of a non-conducting path (as with capacitance measurement) or a current path in the case of a purely resistive path. The lines will be affected by the accretion of ice or other contaminants 338 in proximity of the electrodes. Electrodes 322, 324 are integrated into patch 334 and are comprised of a top layer 342 of conductive resin, a middle layer 344 of conductive cloth and a bottom layer 346 of conductive resin. It is to be noted, however, that although the layers described herein are used for illustrative purposes, and that curing of materials usually results in the materials blending to create structures without clearly defined layers. Electrodes 322, 324 are used to measure ice 338 or other contaminants disposed on the exposed side 339 of detector 310. Patch 334 is preferably an approximately 0.02 inch thick non-conductive urethane film, such as catalog number 121JC202 available from the B.F. Goodrich Company. Guard layer 340 is preferably an approximately 0.003 inch thick copper mesh. Top electrode layer 342 is preferably an approximately 0.003 inch thick layer of conductive urethane resin, such as catalog number 0121JC205 available from the B.F. Goodrich Company. Middle electrode layer 344 is preferably comprised of a nickel coated unidirectional graphite fiber bundle (such as those available from Inco), impregnated with a conductive urethane resin matrix such as catalog number 0121JC205 available from the B.F. Goodrich Company. This graphite fiber bundle consists of a 3K harness and a 50% nickel coating on each filament. Bottom electrode layer 346 is preferably an approximately 0.004 inch thick layer of conductive urethane resin, such as catalog number 0121JC205 available from the B.F. Goodrich Company.

Fabrication of ice detector 310 is as follows.

Roll one ply of raw nonconductive urethane onto a stainless build metal. Vacuum bag and cure at 280° F., 25 psig for 40 minutes.

Mix a conductive urethane by combining a carbon black, such as EC-600 with a urethane cement, such as CP-9 and placing the solution onto a drum roller in a small ball mil for a minimum of 18 hours.

Apply the conductive urethane resin into an aluminum mold with an approximately 0.010 inch cavity provided therein having a width at least as wide as the maximum width of the electrode. Using a sponge brush build up layers at 15 min. intervals until conductive urethane is flush with the surface of the tool. Trim and remove the conductive urethane film from the tool. Lay the film on a stainless build metal. Vacuum bag and cure at 280° F., 25 psig for 40 minutes.

Cut a strip of unidirectional Nickel coated graphite tape to the required length, plus an additional 0.5" for sealing purposes. Tin approximately 0.5" of each end. Dip the entire length of the tape twice with conductive urethane and hang to dry.

Apply the sensor pattern to mylar with 3M77 Spray Adhesive, and trim the template to the required finish size. Lightly spray the mylar with 3M77 Spray Adhesive and position onto the previously cured nonconductive urethane.

Cut out conductive strips through the pattern, mylar and nonconductive urethane. Cut strips of cured conductive urethane to fit into the cutouts in the nonconductive urethane.

Apply the dipped graphite strip in the center to fit the open space in the nonconductive urethane. Cover the graphite strips with another piece of conductive urethane cut to the same size as the first layer. Cut a patch of square woven nylon fabric coated with natural rubber sized to fit under the tinned ends of the graphite strips to reinforce the solder joint.

Solder a conductor lead to each graphite strip. Cover the solder joints with a cover patch of of square woven nylon fabric (same size as patch under the solder joints).

Cover the part with a full size piece of conductive urethane. Bag and cure with Butyl Caul Pad, S-134 to complete the ice detector 310.

An alternate manufacturing procedure can be found in commonly owned U.S. patent application Ser. No. 08/437004, filed May 8, 1995, entitled Ice Detector, now U.S. Pat. No. 5,569,850 the disclosure of which is hereby fully incorporated herein by reference.

Ice detector 310 may then be combined further into a deicer assembly, or it can be utilized as an ice detecting "patch kit" which can be applied almost anywhere on the aircraft. If the ice detector 310 is utilized as a patch kit, the preferred thickness of the non-conductive patch is 0.05 inches thick. An appropriate bonding glue is necessary to bond the patch kit to the aircraft.

Figure 7:
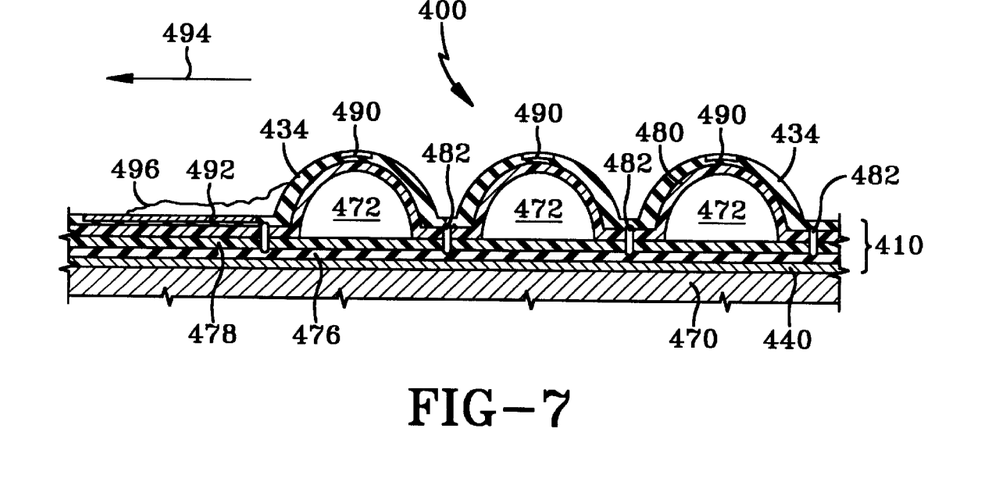
FIG. 7 depicts three ice detector elements imbedded in a deicer boot.

Referring now to FIG. 7, a pneumatic deicing system 400 in accordance with the present invention which includes a deicer assembly 410 comprised substantially of a composite of flexible materials. The deicer assembly 410 is formed as part and parcel of an airfoil skin 470 thereby defining the outer contour of the airfoil. Deicer assembly 410 is typically disposed on the leading edge of the airfoil and is thereby referred to as a leading edge deicer. The preferred method of integrating the deicer assembly 410 with the airfoil 470 is to provide an airfoil, manufacture the deicer assembly as a separate entity, and bond or attach the deicer assembly onto the airfoil at the desired location. The preferred bonding means to attach a deicer assembly 410 to the airfoil 470 is to apply an adhesive, such as catalog number 1300L manufactured by the 3M corporation, to both contacting surfaces.

The principle inflatable portion of the deicer assembly 410 is a plurality of tube-like passages 472 formed therein and arranged substantially parallel to one another in the spanwise direction of the airfoil. Tube-like passages expand or inflate when provided a pressurized fluid, such as air. All inflatable tube-like passages 472 are fluidly connected at one end of deicer assembly 410. The preferred construction for deicer assembly 410 is a composite, comprised from bottom (the side of material bonded to the airfoil) to top of: a) a guard layer 440 such as guard layer 140 described hereinbefore; b) a bottom layer or ply 476 of flexible material, such as neoprene; c) a first intermediate, nonstretchable layer or ply 478 of nonstretchable fabric such as nonstretchable nylon which is rubber coated on one side; c) a second intermediate, layer or ply 480 of stretchable fabric, such as stretchable nylon which is rubber coated one side; and, e) a top layer or ply 434 of a tough yet pliable weather impervious material, such as non-conductive urethane or neoprene. An inflation pattern is created by sewing the nylon layers 478, 480 together in a predetermined pattern using thread 482. The preferred material for thread 482 is nylon or KEVLAR. KEVLAR is a registered trademark of E.I. Dupont Denemours Corporation. Layers 434–480 and 476–478 may be bonded together utilizing an appropriate cement, such as catalog number CHEMLOC 420 manufactured by the Lord Corporation. CHEMLOC is a registered trademark of the Lord Corporation. The inflation pattern consists of a series of high inflation areas or passageways 472, created by stitches 482. Ice detectors 490 similar to ice detectors 110 described hereinbefore are integrated into top layer 434. Detectors 490 are illustrated running substantially in a spanwise direction. An ice detector 492, is also integrated into deicer 410 but runs substantially in a chordwise direction, illustrated by arrow 494. Arrow 494 also illustrates the direction of airflow over deicer 410. Under certain conditions, ice 496 will accumulate chordwise aft of the deicer 410 assembly. This type of accumulation is known in the art as runback ice. It can therefore be seen that ice detector 492 can be utilized to detect runback ice. Of course, deicing patches 490 could be utilized with and integrated into other types of deicing systems or other systems.

Figure 8:
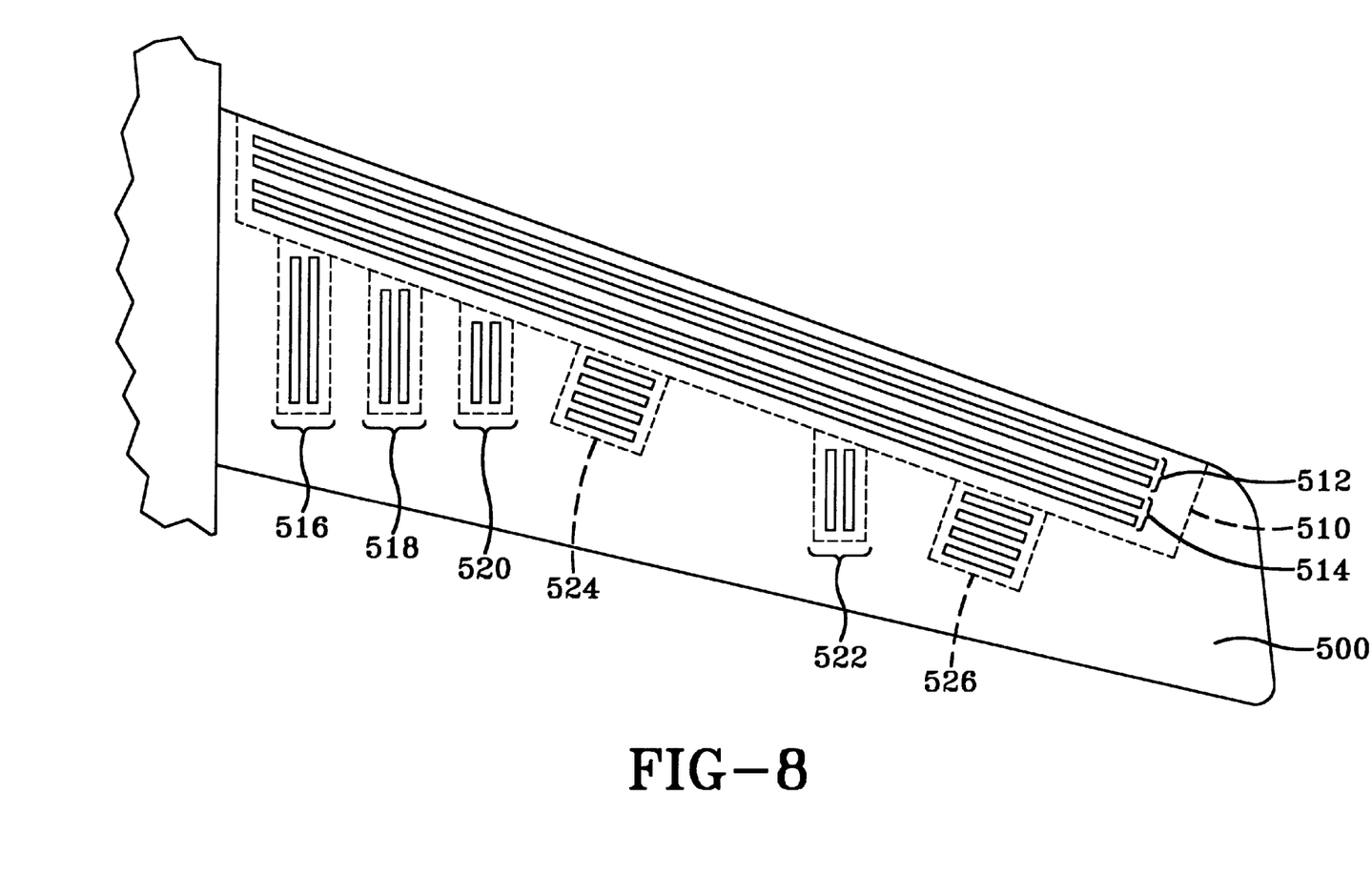
FIG. 8 is a top schematic view of an airfoil having ice detectors in accordance with the present invention.

Referring now to FIG. 8, an airfoil 500 includes a deicer 510. A plurality of electrode pairs 512, 514 (disposed either within deicer 510 or on top of it as a patch) are arranged substantially parallel to each other in the spanwise direction. A plurality of electrodes pairs 516, 518, 520 and 522 are arranged generally in a chordwise direction aft of the deicer 510. A plurality of electrodes groups 524, 526 are also arranged generally in a spanwise direction aft of the deicer 510. It has been found that the present invention facilitates an infinite number of possibilities in the arrangement of the detectors. For instance, one or both electrode pairs 512, 514 may be positioned aft of deicer 510 and one or more of electrode pairs 516–522 may be positioned more chordwise forward than presently shown. The present invention also permits the use of electrodes which can run substantially the entire length of the airfoil, thereby making it possible to "cover" large areas with a single detection circuit. It is to be noted that the preferred electrode construction of the present invention provides electrodes having a length, a width and a thickness, and wherein the length of the electrodes is substantially greater than the width and thickness. The electrodes are disposed at the surface of the airfoil, wherein the length of the electrodes runs substantially parallel to the plane of the airfoil surface. To this end, it is preferred to have the electrodes arranged in parallel pairs, where the electrodes are generally rectangular in cross-section (lengthwise and widthwise) and have a length of on the order of 5 inches, a width of on the order of 0.10 inches, a thickness of on the order of 0.10 inches, and a spacing between the electrodes of on the order of 0.10 inches.

Figure 9:
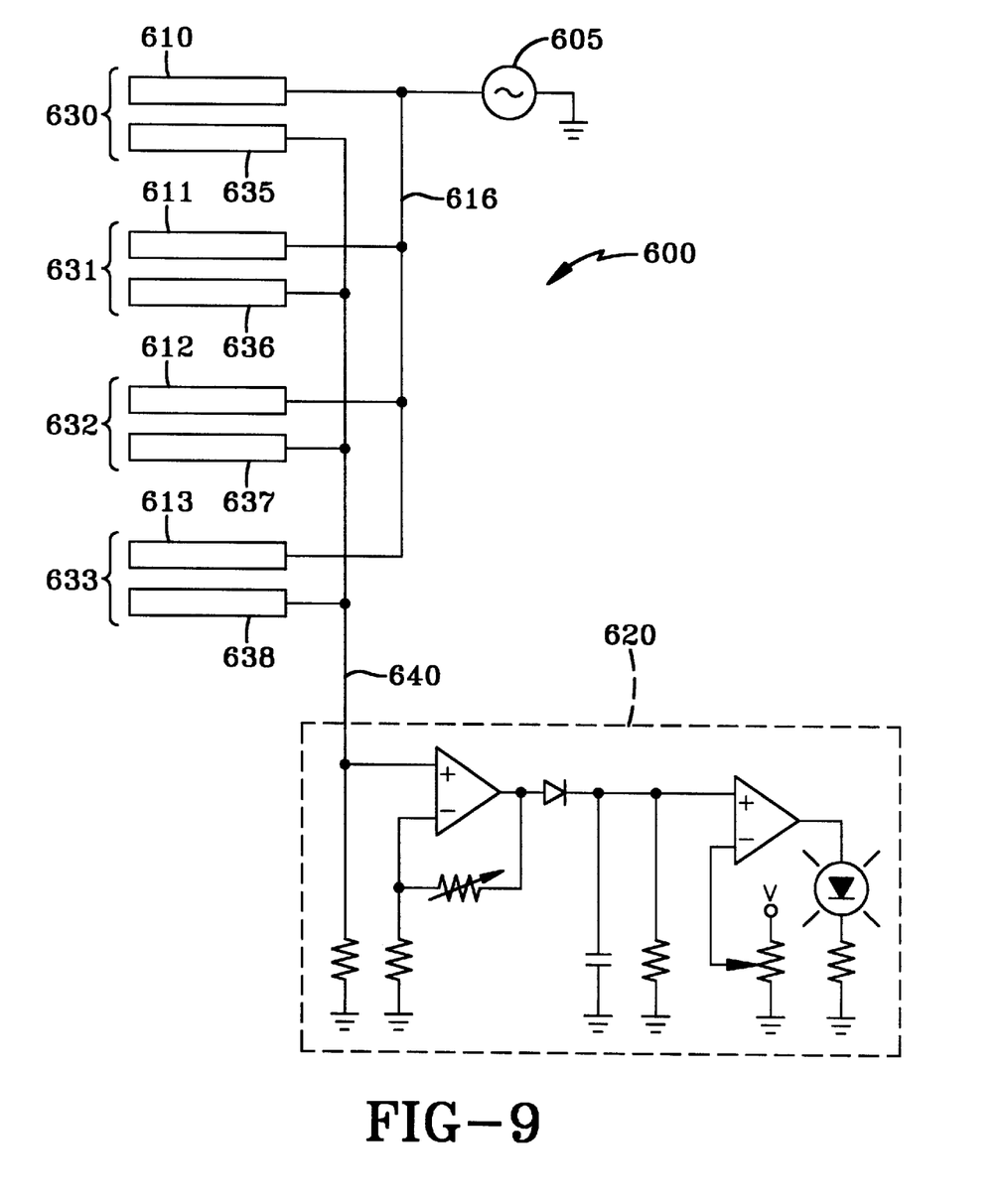
FIG. 9 is a simplified schematic diagram of an alternative embodiment in accordance with the present invention.

Referring now to FIG. 9, an alternate embodiment of an ice detector 600 in accordance with the present invention includes a signal source 605 which drives a plurality of electrodes 610–613 via a line 616. Electrodes 610–613 are part of a plurality of electrode pairs 630–633. Electrodes 635–638 carry return current via a line 640 to an ice detection circuit 620 similar to ice detection circuit 120 described and illustrated hereinbefore in FIG. 4. The electrode pairs 630–633 are thus electrically connected in parallel between signal source 605 and detection circuit 620. Under the present invention, one signal source and one detection circuit can therefore be utilized for a plurality of electrodes, thus providing an ice/no-ice detector at minimal cost.

Figure 10:
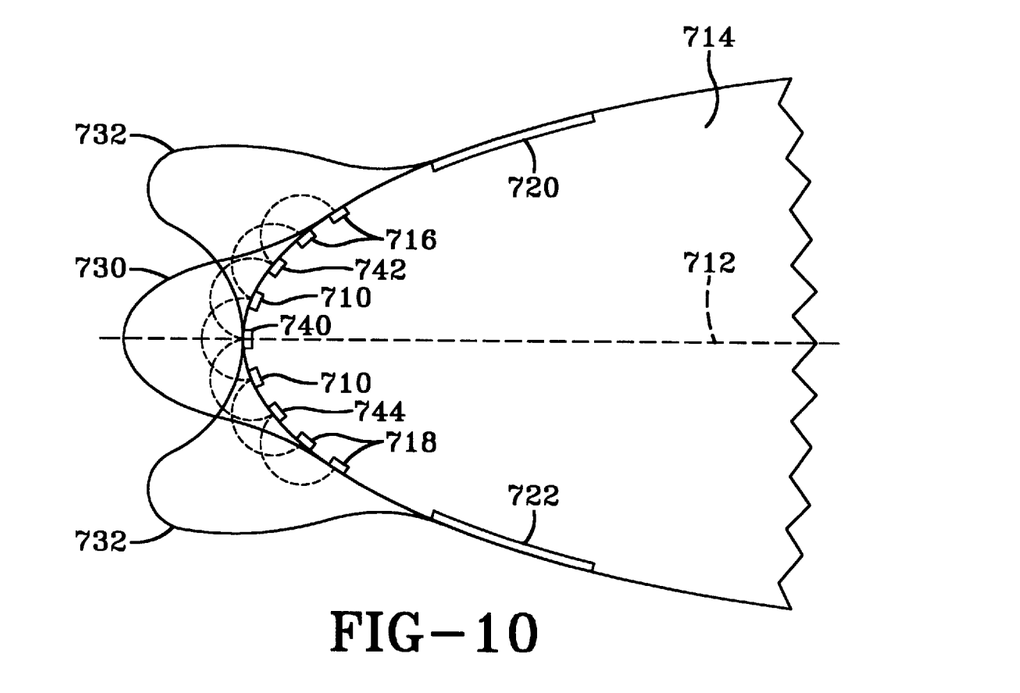
FIG. 10 is a simplified side view of an airfoil having ice detectors in accordance with the present invention.

Referring now to FIG. 10, wherein an ice detection system in accordance with the present invention includes a pair of electrodes 710 arranged in a spanwise direction (so that the substantial length of the electrode is in the plane going into the figure) are located near or at the stagnation line 712 of the airfoil 714. Electrodes 710 are utilized to detect the presence or accumulation of dry growth or rime ice 730 on the airfoil. Electrode pairs 716, 718 are arranged similarly to electrode pair 710 but are disposed at a predetermined chordwise distance off of the stagnation line 712 to detect the presence or accumulation of wet growth, glaze or double horned ice 732 on the airfoil. Alternatively, one electrode 740 may be located near the stagnation line which is coupled to two electrodes 742, 744 off of the stagnation line for detecting the presence of wet growth ice 732. Electrodes 720, 722 are arranged in a chordwise direction (so that the substantial length of the electrode is in the plane of the figure) and are disposed at a predetermined chordwise distance off of the stagnation line 712 to detect the presence or accumulation of runback ice. Electrodes 720, 722 presumably would be at least partially positioned behind any deicing equipment installed on the airfoil. Since the stagnation line 712 changes with airfoil configuration and angle of attack, the exact position of the electrodes will have to optimized for different airfoils and operating characteristics.

Figure 11:
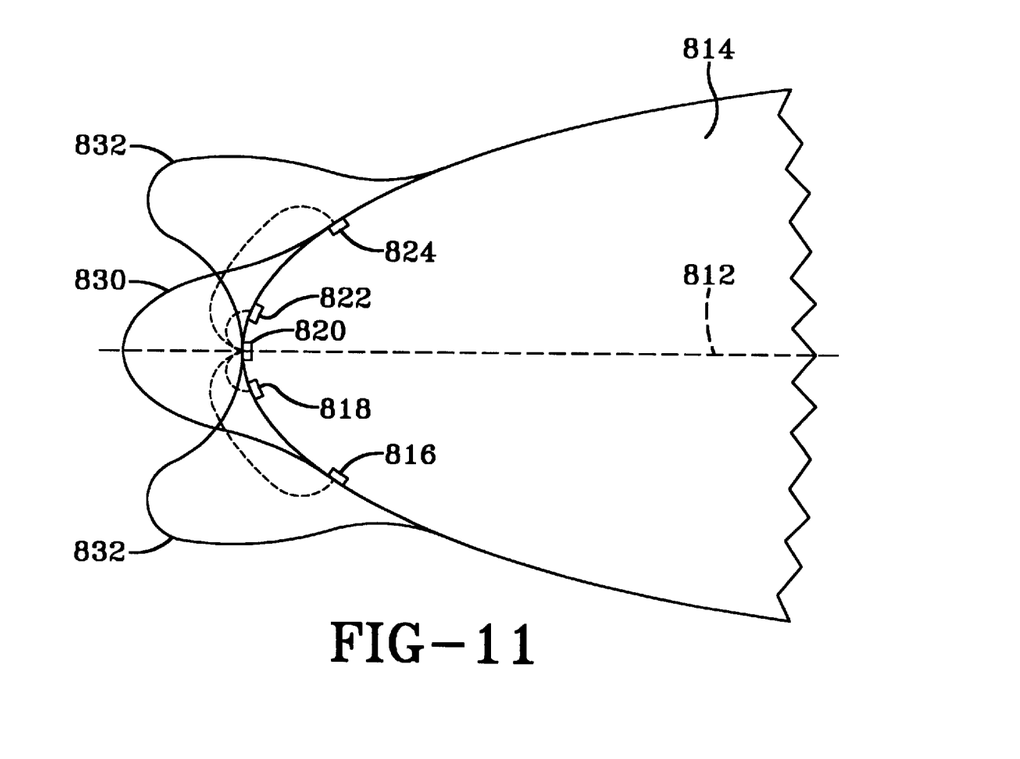
FIG. 11 is a simplified side view of an airfoil having ice detectors in accordance with the present invention.

Referring now to FIG. 11, wherein an ice detection system in accordance with the present invention includes a plurality of electrodes 816–824 arranged in a spanwise direction (so that the substantial length of the electrode is in the plane going into the figure) are located near or at the stagnation line 812 of the airfoil 814. Electrodes 816–824 are utilized to detect the presence or accumulation of ice on the airfoil. Measurement from electrode 820 to electrodes 818 and 822 will detect the presence of rime ice 830. Measurement from electrode 820 to electrodes 816 and 824 will detect the presence of glaze ice 832. Alternatively, measurement can be taken from electrode 820 to 816, 818, 822 and 824 simultaneously.

Figure 12A:
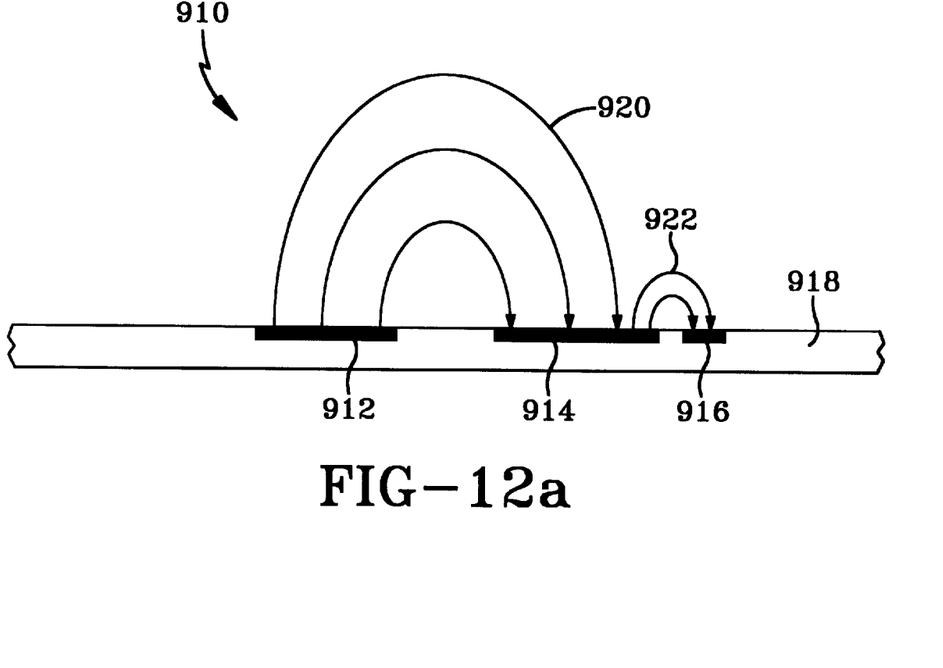
FIG. 12a is a cross sectional view of ice detector electrodes in an ice detection patch in accordance with an alternative embodiment of the present invention.
Figure 12B:
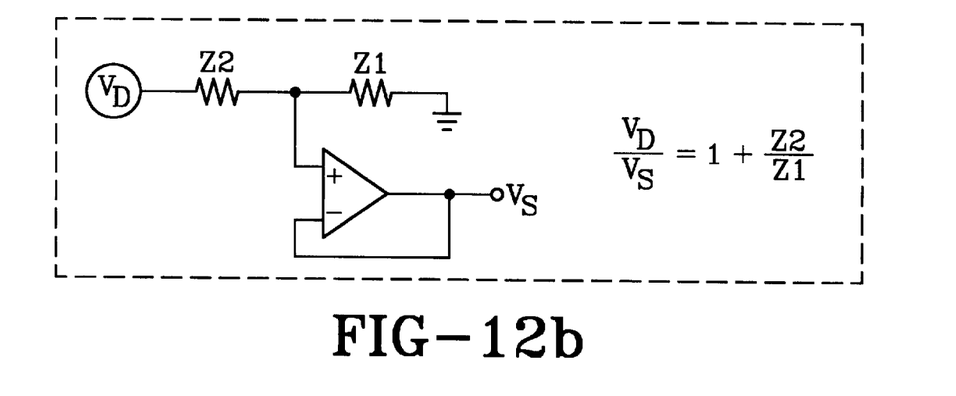

Referring now to FIG. 12a and 12b, an alternative detector 910 for determining the thickness of ice accredited on the leading edge of an airfoil independent of ice composition includes a drive electrode 912, a floating electrode 914 and a ground electrode 916 imbedded in a structure 918. Lines 920, 922 represent the electric fields between the electrode. Two different sized electrical sensors are used to infer the ice thickness. The first sensor, Type 1 comprised of electrodes 914 and 916, is configured to have electric field lines that extend roughly 0.1" into the ice while the latter sensor, Type 2 comprised of electrodes 912 and 914, uses a different geometry to generate field lines that penetrate 0.5" into the ice. The electrodes are driven by a source similar to that described hereinbefore. The output of either sensor is proportional to the quantity of ice over the sensor and to the composition of the ice and thus neither one on its own can be used to infer ice thickness for all types of ice. The composition of the ice is compensated for by dividing the output of the Type 2 sensor by the output from the Type 1. Once the ice has exceeded 0.1 inches thick and the Type 1 sensor has saturated the divided output is only a function of the ice thickness.

The measurement electronics (not shown but similar to electronics described hereinbefore) are designed to measure the complex impedance of the ice which includes both the resistance and the capacitive impedance. As discussed before, the use of complex impedance is a more robust technique in that the measurement incorporates both the capacitive reactance for when the ice conductivity is low and the resistance for when the ice conductivity is high. This method allows for the determination of ice thickness for all types of ice.

The configuration in FIG. 12 a can be described as a single Type 3 sensor which incorporates a drive electrode 912, floating sense electrode 914, and ground electrode 916. FIG. 12b shows a schematic representation of the sensor 910. The drive electrode is connected to an oscillator which generates a sinusoidal signal at a fixed frequency and amplitude. Current from the drive electrode is conducted to the floating sense electrode through impedance Z2 which essentially forms the Type 2 element of the sensor. The current then continues on to the ground electrode through impedance Z1 which forms the Type 1 element. These two impedance paths generate a series circuit comprised of impedance Z2, and impedance Z1, as shown in the equivalent circuit. This is well known as a voltage dividing circuit. The ratio of the drive voltage $V_D$ to the measured sense voltage $V_S$ is equal to 1.0 plus the ratio of Z2 divided by Z1. This last quantity is the ratio needed for the ice thickness algorithm discussed above. With this new embodiment of the Type 2 divided by Type 1 ice thickness system the required sensor and electronics are dramatically simplified. The associated electronics would calculate the ratio and provide a simplified thickness detector.

Although the invention has been shown and described with exemplary embodiments thereof, it should be understood by those skilled in the art that the foregoing and various other changes, omissions and additions may be made therein and thereto without departing from the spirit and the scope of the invention.

Figure 13:
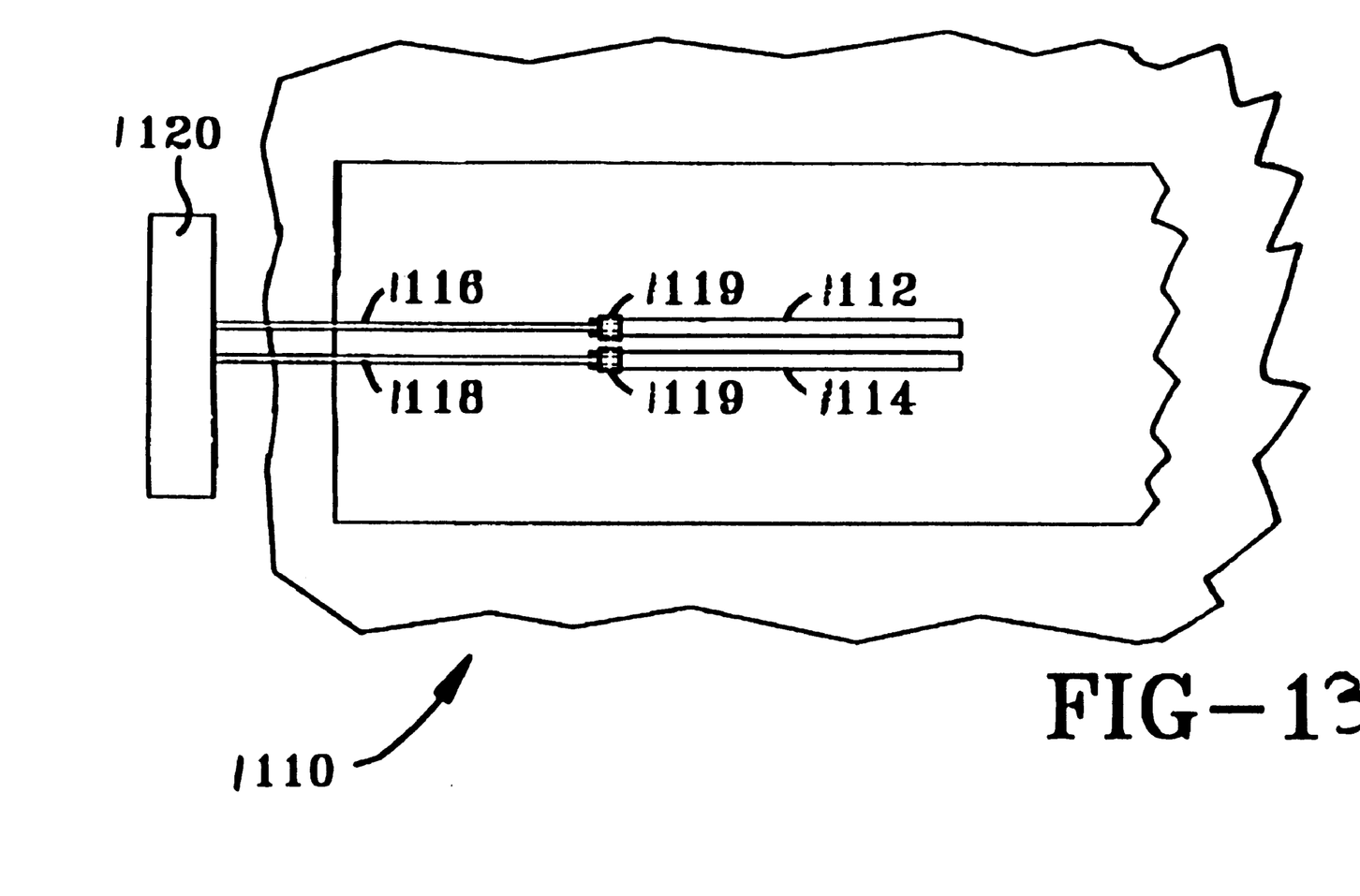
FIG. 13 is a top view of an ice detector in accordance with an additional embodiment of the present invention.

Referring now to FIG. 13, an ice detector 1110 in accordance with the present invention includes a first pair of electrodes, or elements, 1112, 1114 connected by a pair of leads 1116, 1118 to a controller or control unit 1120. Control unit 1120 measures the impedance between leads 1116 and 1118. Control unit 1120 may also measure other parameters such as capacitance required to sense and detect ice or other contaminates formed on top of detector 1110. It is to be noted that controller 1120 may be any of a number of controller which measure impedance or capacitance known to those skilled in the art, such as those described in the heretofore mentioned U.S. Pat. No. 4,766,369 to Weinstein and 5,398,547 to Girardi et al, hereby incorporated herein by reference.

We claim:

1. An apparatus for detecting ice on a surface of an aircraft exposed to the environment comprising:

first, second and third electrodes disposed at the exposed surface of the aircraft, the electrodes being spaced apart and arranged substantially parallel to the plane of the surface, wherein the second electrode is spaced closer to the first electrode than the third electrode;

a signal driver for applying a drive signal to the first electrode;

a first device for providing a first signal indicative of the current flowing through the second electrode;

a second device for providing a second signal indicative of the current flowing through the second electrode; and, a third device for determining the difference between the second and third signal.

2. An apparatus in accordance with claim 1, wherein the apparatus operates while the aircraft is in operation.

3. A method of detecting ice on the surface of an aircraft comprising the steps of:

providing first, second and third electrodes disposed at the exposed surface of the aircraft, the electrodes being spaced apart and arranged substantially parallel to the plane of the surface, wherein the second electrode is spaced closer to the first electrode than the third electrode;

applying a signal to the first electrode;

providing a first signal indicative of the current flowing through the second electrode;

providing a second signal indicative of the current flowing through the second electrode; and, determining the difference between the second and third signal.

4. A method of detecting ice on the surface of an aircraft in accordance with claim 3, wherein the steps are performed while the aircraft is in operation.

5. A method of detecting ice on the surface of an aircraft comprising the steps of:

providing first, second and third electrodes disposed at the exposed surface of the aircraft, the electrodes being spaced apart and arranged substantially parallel to the plane of the surface, wherein the second electrode is spaced closer to the first electrode than the third electrode;

applying a signal to the first electrode;

providing a first signal indicative of the current flowing through the second electrode;

providing a second signal indicative of the current flowing through the second electrode; and, correlating the thickness of the ice on the surface with a determination of when the second and third signals are equal.

6. A method of detecting ice on the surface of an aircraft in accordance with claim 5, wherein the steps are performed while the aircraft is in operation.

* * * * *